United States Patent [19]

Whittle

[11] Patent Number: 4,902,814

[45] Date of Patent: Feb. 20, 1990

[54] FLUOROBENZYL ESTERS

[75] Inventor: Alan J. Whittle, Hampshire, England

[73] Assignee: Imperial Chemical Industries PLC, London, England

[21] Appl. No.: 69,443

[22] Filed: Jul. 2, 1987

[30] Foreign Application Priority Data

Jul. 18, 1986 [GB] United Kingdom ............... 8617649

[51] Int. Cl.$^4$ .................... C07C 122/00; C07C 33/03; C07C 19/08; C07C 21/24
[52] U.S. Cl. ..................... 558/388; 558/410; 568/809; 570/128; 570/129; 560/105; 560/124
[58] Field of Search .......... 558/407, 410, 388; 560/124, 105; 568/812, 809; 570/129, 128; 514/531, 546, 751, 730

[56] References Cited

U.S. PATENT DOCUMENTS

| | | | |
|---|---|---|---|
| 4,024,163 | 5/1977 | Elliott et al. | 560/124 |
| 4,225,533 | 9/1980 | Henrick | 560/124 |
| 4,457,940 | 7/1984 | Katsuda et al. | 560/124 |
| 4,661,488 | 4/1987 | McDonald et al. | 560/124 |

FOREIGN PATENT DOCUMENTS

| | | | |
|---|---|---|---|
| 0060617 | 9/1982 | European Pat. Off. | 560/124 |
| 0156630 | 10/1985 | European Pat. Off. | 560/124 |
| 2108123 | 5/1983 | United Kingdom | 560/124 |
| 2157288 | 10/1985 | United Kingdom | 560/124 |
| 2178739 | 2/1987 | United Kingdom | 560/124 |

Primary Examiner—Mary C. Lee
Assistant Examiner—Robert C. Whittenbaugh
Attorney, Agent, or Firm—Cushman, Darby & Cushman

[57] ABSTRACT

A compound of formula:

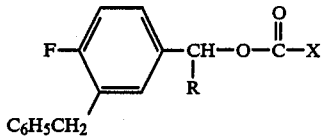

wherein R is selected from hydrogen, cyano, methyl, and ethynyl, and X represents the residue of any carboxylic acid of formula X-COOH which forms an insecticidally active ester with a 3-phenoxybenzyl alcohol. The compounds are useful as insecticides and acaricides.

7 Claims, No Drawings

FLUOROBENZYL ESTERS

This invention relates to novel fluorobenzyl esters useful as insecticides and acaricides, and to intermediates and processes useful in their preparation.

The novel fluorobenzyl esters of this invention have the general formula (I)

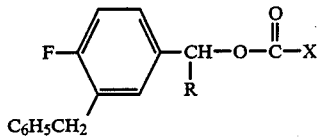
(I)

wherein R is selected from hydrogen, cyano, methyl and ethynyl, and X represents the residue of any carboxylic acid of formula X-COOH which forms an insecticidally active ester with a 3-phenoxybenzyl alcohol. More particularly X represents (a) a group of formula:

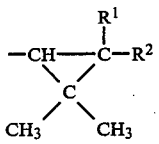

wherein (i) $R^1$ and $R^2$ are each selected from hydrogen, halo and alkyl of up to four carbon atoms; or (ii) $R^1$ is hydrogen and $R^2$ represents either a group of formula:

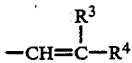

or a group of formula:

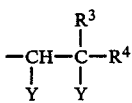

where $R^3$ and $R^4$ are each selected from methyl, halo, or haloalkyl of one or two carbon atoms containing at least two fluorine atoms, and Y is chloro or bromo; or (iii) $R^1$ is hydrogen and $R^2$ represents a group of formula

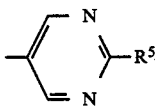

where $R^5$ represents an al-pha-branched alkyl group; or (b) X represents a group of formula:

where $R^6$ represents an alkyl group of up to four carbon atoms and Ar represents a phenyl group optionally substituted with one or two halogen atoms.

Preferred compounds according to the invention are those of formula (IA):

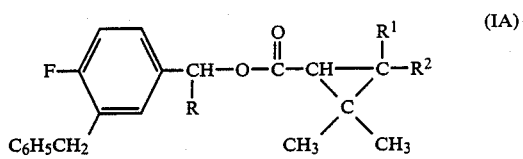
(IA)

wherein R is hydrogen, cyano or methyl, $R^1$ and $R^2$ are each selected from halogen-and alkyl of up to four carbon atoms (preferably methyl), or $R^1$ is hydrogen and $R^2$ is a group of formula:

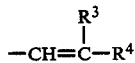

wherein $R^3$ and $R^4$ are each selected from methyl, fluoro, chloro, bromo and trifluoromethyl, or $R^1$ is hydrogen and $R^2$ is a group of formula

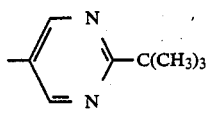

Particularly preferred compounds according to formula (I) are those set out in Table I below wherein the meanings of $R^1$ and $R^2$ are set out for each compound.

TABLE I

| Compound | R | $R^1$ | $R^2$ |
|---|---|---|---|
| 1 | H | $CH_3$ | $CH_3$ |
| 2 | H | H | $-CH=C(CH_3)_2$ |
| 3 | H | H | $-CH=CCl_2$ |
| 4 | H | H | $-CH=CBr_2$ |
| 5 | H | H | $-CH=CF_2$ |
| 6 | H | H | $-CH=C(F)CF_3$ |
| 7 | H | H | $-CH=C(Cl)CF_3$ |
| 8 | H | H | $-CH=C(Br)CF_3$ |
| 9 | H | H | $-CH=C(CF_3)_2$ |
| 10 | H | Cl | Cl |
| 11 | CN | $CH_3$ | $CH_3$ |
| 12 | CN | H | $-CH=C(CH_3)_2$ |
| 13 | CN | H | $-CH=CCl_2$ |
| 14 | CN | H | $-CH=CBr_2$ |
| 15 | CN | H | $-CH=CF_2$ |
| 16 | CN | H | $-CH=C(F)CF_3$ |
| 17 | CN | H | $-CH=C(Cl)CF_3$ |
| 18 | CN | H | $-CH=C(Br)CF_3$ |
| 19 | CN | H | $-CH=C(CF_3)_2$ |
| 20 | CN | Cl | Cl |
| 21 | $CH_3$ | $CH_3$ | $CH_3$ |
| 22 | $CH_3$ | H | $-CH=C(CH_3)_2$ |
| 23 | $CH_3$ | H | $-CH=CCl_2$ |
| 24 | $CH_3$ | H | $-CH=CBr_2$ |
| 25 | $CH_3$ | H | $-CH=CF_2$ |
| 26 | $CH_3$ | H | $-CH=C(F)CF_3$ |
| 27 | $CH_3$ | H | $-CH=C(Cl)CF_3$ |
| 28 | $CH_3$ | H | $-CH=C(Br)CF_3$ |
| 29 | $CH_3$ | H | $-CH=C(CF_3)_2$ |
| 30 | $CH_3$ | Cl | Cl |
| 31 | $-C\equiv CH$ | H | $-CH=C(CH_3)_2$ |
| 32 | $-C\equiv CH$ | H | $-CH=CCl_2$ |
| 33 | $-C\equiv CH$ | H | $-CH=CBr_2$ |
| 34 | $-C\equiv CH$ | H | $-CH=C(Cl)CF_3$ |
| 35 | $-C\equiv CH$ | H | $-CH=C(F)CF_3$ |
| 36 | H | H | 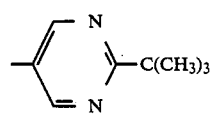 |

TABLE I-continued

| Compound | R | R¹ | R² |
|---|---|---|---|
| 37 | CN | H | 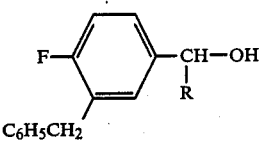 |

Many of the compounds according to the invention are capable of existing in more than one isomeric form owing to the presence of one or more asymmetrically substituted carbon atoms. This, in those compounds of formula I wherein R is not hydrogen, the asymmetrically substituted carbon atom to which R is attached may exist in the R-form or the S-form. Asymmetric substitution is also exhibited at the $C_1$ carbon atom of the cyclopropane ring of the compounds of formula (IA) when $R^1$ and $R^2$ are not both methyl, and additionally at the $C_3$ atom where $R^1$ and $R^2$ are not identical. In the latter case, four isomeric forms of the acid moiety may exist, the (1R,cis), (1S,cis), (1R,trans) and (1S,trans) forms.

Where $R^3$ and $R^4$ are not identical there exists the further possibility of E and Z isomers of the group $R^2$. The scope of the invention includes each of the said isomeric forms in isolation as well as mixtures thereof, including racemic mixtures.

Especially preferred compounds according to formula (I) include the 3-benzyl-4-fluorobenzyl, 3-benzyl-α-cyano-4-fluorobenzyl and 3-benzyl-α-methyl-4-fluorobenzyl esters of the following cyclopropane acids.
2,2,3,3-tetramethylcyclopropanecarboxylic acid,
2,2-dichloro-3,3-dimethylcyclopropanecarboxylic acid,
(1RS,cis)-3-(2,2-dichlorovinyl)-2,2-dimethylcyclopropanecarboxylic acid,
(1RS,trans)-3-(2-methylprop-1-en-1-yl)-2,2-dimethylcyclopropanecarboxylic acid,
(1RS,cis)-3-(2,2-difluorovinyl)-2,2-dimethylcyclopropanecarboxylic acid,
(1RS,cis)-3-(2,2-dibromovinyl)-2,2-dimethylcyclopropanecarboxylic acid,
(1R,cis)-3-(2,2-dibromovinyl)-2,2-dimethylcyclopropanecarboxylic acid,
(1RS,cis)-3-(Z-2-chloro-3,3,3-trifluoroprop-1-en-1-yl)-2,2-dimethylcyclopropanecarboxylic acid,
(1R,cis)-3-(Z-2-chloro-3,3,3-trifluoroprop-1-en-1-yl)-2,2-dimethylcylcopropanecarboxylic acid,
(1RS,cis)-3-(Z-2,3,3,3-tetrafluoroprop-1-en-1-yl)-2,2-dimethylcyclopropanecarboxylic acid,
(1RS,trans)-3-(Z-2,3,3,3-tetrafluoroprop-1-en-1-yl)-2,2-dimethylcyclopropanecarboxylic acid,
(1RS,cis)-3-(2-trifluoromethyl-3,3,3-trifluoroprop-1-en-1-yl)-2,2-dimethylcyclopropanecarboxylic acid, and
(1RS,trans-3-[2-(1,1-dimethylethyl)pyrimidin-5-yl]-2,2-dimethylcyclopropanecarboxylic acid.

Other compounds of the invention include the 3-benzyl-4-fluorobenzyl and 3-benzyl-α-cyano-4-fluorobenzyl esters of:
(1RS,cis)-3-(1,2-dibromo-2,2-dichloroethyl)-2,2-dimethylcyclopropanecarboxylic acid and (RS)-2-(4-chlorophenyl)-3-methylbutyric acid.

The compounds of the invention are esters and may be prepared by conventional esterification processes, of which the following are examples.

(a) An acid of formula (II)

$$X\text{—COOH} \quad (II)$$

where X has any of the meanings given hereinabove, may be reacted directly with a fluorobenzyl alcohol of formula (III):

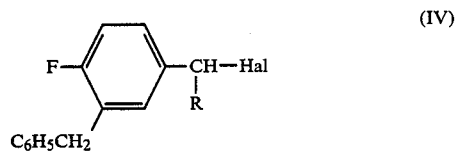

wherein R has, any of the meanings given hereinabove, the reaction preferably taking place in the presence of an acid catalyst, for example, dry hydrogen chloride, or a dehydrating agent, for example, a carbodiimide such as dicyclohexylcarbodiimide.

(b) An acid halide of formula X-COHal where Hal represents a halogen atom, preferably a chlorine atom, and X has any of the meanings given hereinabove, may be reacted with an alcohol of formula (III), the reaction preferably taking place in the presence of a base, for example, pyridine, trialkylamine, alkali metal hydroxide or carbonate, or alkali metal alkoxide.

In a variant of this process leading to the formation of α-cyano substituted esters, an acid halide of formula X-COHal is reacted with 3-benzyl-4-fluorobenzyldehyde (V) in the presence of an alkali metal cyanide, the reaction preferably taking place in a two phase system in which the cyanide is dissolved in water, with the assistance of a phase transfer catalyst such as a tetraalkyl ammonium halide, for example tetraethyl ammonium chloride.

(c) An acid of formula (II) where X has any of the meanings given hereinabove, or preferably, an alkali metal salt thereof, may be reacted with a halide of formula (IV):

$$\text{(IV)}$$

where R is as defined hereinabove and Hal represents a halogen atom, preferably the bromine or chlorine atom, or with the quaternary ammonium salts derived from such halides with tertiary amines, for example pyridine or trialkylamines such as triethylamine.

(d) A lower alkyl ester of formula X-COOQ where Q represents a lower alkyl group containing up to six carbon atoms, preferably the methyl or ethyl group, and X has any of the meanings given hereinabove, is heated with an alcohol of formula (III) to effect a trans-esterification reaction. Preferably the process is performed in the presence of a suitable catalyst, for example, an alkali metal alkoxide such as sodium methoxide, or an alkylated titanium derivative such as tetramethyl titanate or tetraethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example, phase-transfer catalysts.

The preparation of individual isomers may be carried out in the same manner but commencing from the corresponding individual isomers of compounds of formula (II). These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the alcohol of formula (II) to produce a compound of formula I in the form of an individually pure isomer thereof.

Esterifiable derivatives of the acids of formula (II) wherein X represents the group of formula:

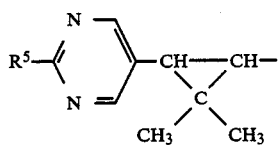

wherein $R^5$ represents an α-branched alkyl group, are described in UK Patent Application No. 2,157,288A.

The compounds of formula (III) and (IV) and 3-benzyl-4-fluorobenzaldehyde have not been described previously. In a further aspect therefor the invention provides compounds of formula (III) and (IV) and more specifically each of the following compounds:
3-benzyl-4-fluorobenzyldehyde
3-benzyl-4-fluorobenzyl alcohol
α-cyano-3-benzyl-4-fluorobenzyl alcohol
3-benzyl-4-fluorobenzyl chloride
α-cyano-3-benzyl-4-fluorobenzyl chloride
α-methyl-3-benzyl-4-fluorobenzyl alcohol
α-methyl-3-benzyl-4-fluorobenzyl chloride.

3-Benzyl-4-fluorobenzaldehyde may be prepared by means of the process described in Scheme I. The compounds of formula (III) and formula (IV) May be prepared from 3-benzyl-4-fluorobenzaldehyde by means of the processes described in Scheme II. Further details of many of these processes are given in the Examples hereinafter.

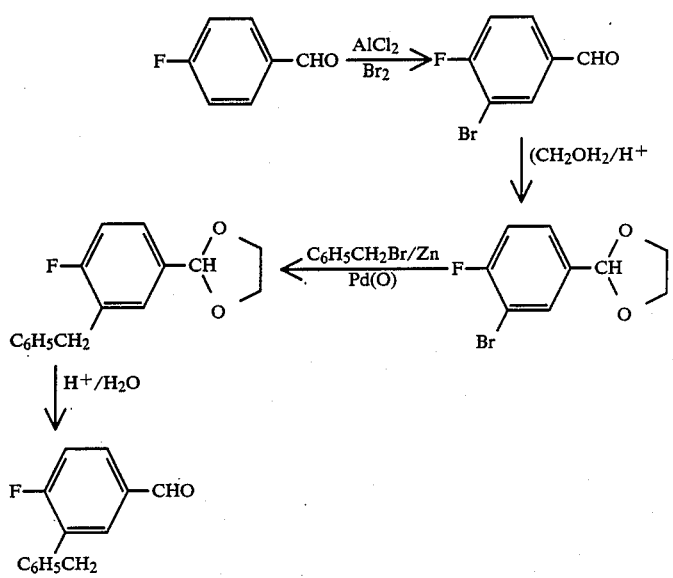

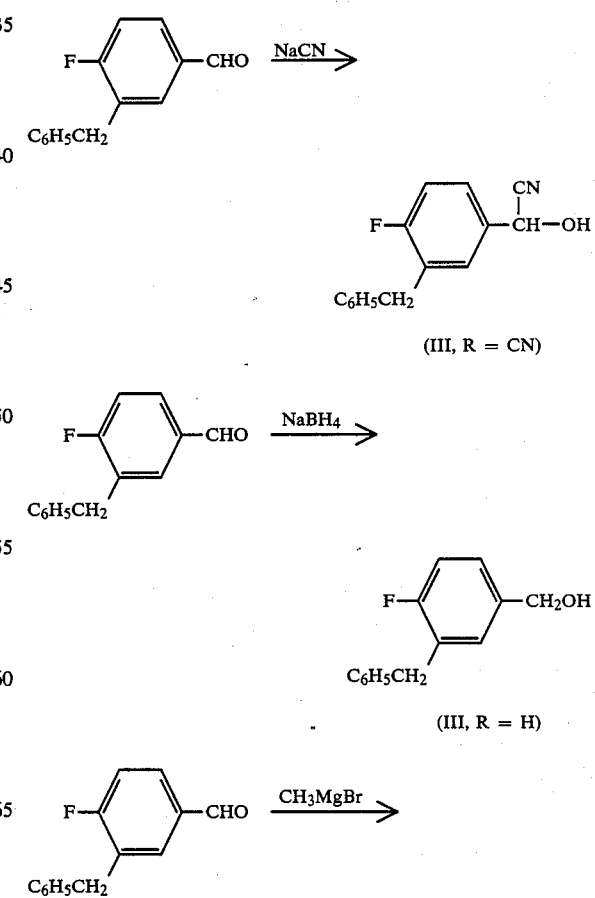

-continued
Scheme II

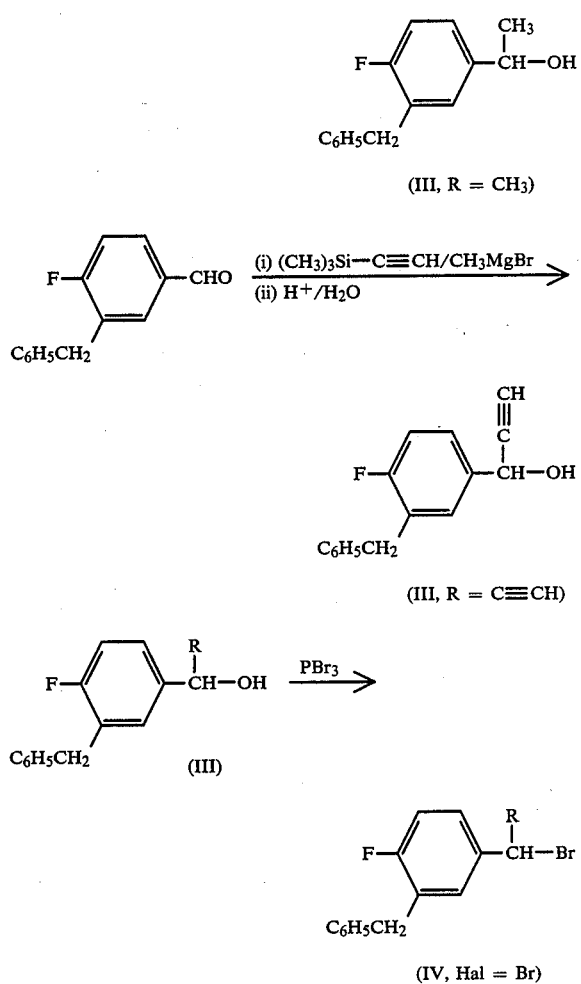

The compounds of formula (I) may be used to combat and control infestations of insect and acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredients of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphosmethyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones such as juvenile hormone, juvabione, or ecdysones.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 5-95% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of formula (I) and compositions comprising them are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitos)
*Anopheles* spp. (mosquitos)
*Culex* spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Aonidiella* spp. (scale insects)
*Trialeuroides* spp. (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
*Diabrotica* spp. (rootworms)
*Agrotis* spp. (cutworms)
*Chilo partellus* (maize stem borers)
*Nilaparvata lugens* (plant hoppers)
*Nephotettix cincticeps* (plant hoppers)

The compounds of formula (I) and compositions comprising them have shown themselves to be useful in controlling foliar feeding pests of plants, and public health pests such as flies and mosquitos. The compounds may also be used to combat pests which inhabit the soil, for example Diabrotica spp. They may also be useful in combating insect and acarine pests which infest domestic animals, such as Lucilia ericata, and ixodid ticks such as Boophilus spp., Ixodes spp., Amblyomma spp., Rhipicephalus spp., and Dermaceutor spp. They are expected to be effective in combating both susceptible and resistant strains of these pests in their adult, larval and intermediate stages of growth, and may be applied to the infested host animal by topical, oral or parenteral administration.

The compounds according to formula (I) and compositions comprising them also exhibit a high level of acaricidal activity, and are particularly useful in the control of the following acarine pests:

Panonychus spp., for example *Panonychus ulmi* and *Panonychus citri;*
Tetranychus spp., for example *Tetranychus urticae* and *Tetranychus cinnabarinus;*
*Phyllocoptruta oleivora;*
Polyphagotarsonemus spp., and
Brevipalpus spp.

The following Examples illustrate various aspects of this invention. In the preparation Examples the products were usually identified and characterised by means of nuclear magnetic reasonance spectroscopy and infra red spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chromopak, C.P. Sil 5 C.B. column of 12.5M length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz 1H NMR spectrometry were performed using Jeol FX 90Q, Jeol PMX 60SI ad Jeol GX400 spectrometers respectively.

$^{19}$F NMR spectrometry was performed on a Jeol FX90Q spectrometer at a frequency of 84.26 MHz. All NMR shift ($\delta$) values are quoted in ppm relative to a standard (TMS or CFCl$_3$)

Molecular Ion (M+) peaks were determined on one of three mass spectrometers: Jeol DX303, Kratos MS80 or Hewlett Packard HP 5992.

EXAMPLE 1

This Example illustrates the stages in the preparation of 3-benzyl-4-fluorobenzyl alcohol.

Stage 1: Preparation of 3-bromo-4-fluorobenzaldehyde.

A solution of 4-fluorobenzaldehyde (49.6 g) in dry dichloromethane (20 cm$^3$) was added to a cooled (0° C.) suspension of powdered aluminium trichloride (90.4 g) in dry dichloromethane (100 cm$^3$). Bromine (70.4 g) was added, and the mixture heated at the reflux temperature for 16 hours. After cooling, the reaction mixture was carefully poured onto ice and extracted with dichloromethane. The combined organic layers were washed with saturated sodium metabisulphite solution, water and brine, then dried over anhydrous magnesium sulphate. Evaporation of the solvent under reduced pressure gave a dark red oil, which was purified by distillation under reduced pressure, using a 4" Vigreux column to give 3-bromo-4-fluorobenzaldehyde (45.7 g) as an oil, boiling point 85°–108° C. at 8 mmHg.

Stage 2: Preparation of 2-(3-bromo-4-fluorophenyl)-1,3-dioxolane.

A mixture of 3-bromo-4-fluorobenzaldehyde (45.7 g), ethylene glycol (27.39 g), p-toluenesulphonic acid (0.225 g) and dry toluene (110 cm$^3$) was heated at the reflux temperature under a Dean and Stark trap. After 4.5 hours, approximately 12 cm$^3$ of water had collected in the trap, and analysis of the reaction mixture by gas liquid chromatography indicated that no starting aldehyde was present. The cooled mixture was washed with sodium bicarbonate solution and brine, and dried over anhydrous magnesium sulphate. Evaporation of the solvent under reduced pressure gave a yellow oil, which was purified by distillation under reduced pressure to give 2-(3-bromo-4-fluorophenyl)-1,3-dioxolane (43.56 g), boiling point 68°–106° C. at 0.004 mmHg.

90 MHz $^1$H NMR (CDCl$_3$) (ppm): 4.1 (4H,m); 5.8 (1H,s); 7.0–7.7 (3H,m).

Stage 3: Preparation of 2-(3-benzyl-4-fluorophenyl)-1,3-dioxolane.

This compound was prepared by a method analogous to that reported by Minato et al in Tetrahedron Letters, 21, p845, (1980).

Benzyl bromide (2.77 g) was added in one addition to a suspension of activated zinc powder (2.1 g) in dry tetrahydrofuran (20 cm$^3$) under an atmosphere of nitrogen. The reaction mixture was sonicated for 2 hours, allowed to stand for 30 minutes and carefully filtered under an atmosphere of nitrogen. The filtered solution was then added to a mixture of 2-(3-bromo-4-fluorophenyl)-1,3-dioxolane (1 g) and palladium (O) tetrakis triphenylphosphine (0.05 g) in dry tetrahydrofuran (10 cm$^3$) under an atmosphere of nitrogen. The stirred mixture was heated at the reflux temperature for 48 hours, at which time analysis by gas liquid chromatography showed no trace of starting material. The reaction mixture was cooled and poured into diethyl ether. The organic layer was separated and washed with ammonium chloride solution, water and brine, then dried over anhydrous magnesium sulphate. Evaporation of the solvent under reduced pressure gave a yellow oil which was purified by column chromatography on a silica gel support, using petroleum ether (boiling range 40°–60° C.) containing diethyl ether (progressively increased from 10% to 20% by volume) as eluent to give 2-(3-benzyl-4-fluorophenyl)-1,3-dioxolane (0.7 g). The product was used without further purification.

60 HMz $^1$H NMR (CDCl$_3$) (ppm): 4.0 (6H,m); 5.7 (1H,s); 6.8–7.5 (8H,m).

Stage 4: Preparation of 3-benzyl-4-fluorobenzaldehyde.

A mixture of 2-(3-benzyl-4-fluorophenyl)-1,3-dioxolane (0.7 g), acetone (10 cm$^3$), water (1 cm$^3$) and concentrated sulphuric acid (5 drops) was stirred for 16 hours. The reaction mixture was poured into diethyl ether and the organic layer washed with sodium bicarbonate solution, water and brine, then dried over anhydrous magnesium sulphate. Evaporation of the solvents under reduced pressure gave 3-benzyl-4-fluorobenzaldehdye (0.59 g), which was used without further purification.

$^1$H NMR (CDCl$_3$) (ppm): 4.10 (2H,s); 7.20 (6H,m); 7.75 (2H,m); 9.90 (1H,s).

IR (liquid film): 1700 cm$^{-1}$ (C=O).

Stage 5: Preparation of 3-benzyl-4-fluorobenzyl alcohol.

A solution of 3-benzyl-4-fluorobenzaldehyde (5 g) in methanol (75 cm$^3$) was cooled to 0° C. Sodium borohydride (1.34 g) was added in portions, and the mixture stirred for 1 hour. The reaction mixture was then poured cautiously into a mixture of water and diethyl ether, and the organic layer was separated, washed with water and brine, and dried over anhydrous magnesium sulphate. Evaporation of the solvents under reduced pressure gave a pale yellow oil which was purified by distillation in a kugelrohr apparatus to give 3-benzyl-4-fluorobenzyl alcohol (4.0 g).

Boiling point: 120° C. at 0.02 mmHg.

$^1$H NMR (CDCl$_3$) (ppm): 1.7 (1H,broad s); 4.0 (2H,s); 4.6 (2H,s); 7.0–7.3 (8H,m).

IR (liquid film): 3600–3100 cm$^{-1}$ (OH).

EXAMPLE 2

This Example illustrates the preparation of 3-benzyl-4-fluorobenzyl (1RS, cis)-3-(Z-2-chloro-3,3,3-trifluoroprop-1-en-1-yl)-2,2-dimethylcyclopropane carboxylate (Product I).

A solution of dicyclohexylcarbodiimide (0.4 g) in dichloromethane (10 cm$^3$) was added to a stirred mixture of (1RS, cis)-3-(Z-2-chloro,3,3,3-trifluoroprop-1-en-1-yl)-2,2-dimethylcyclopropanecarboxylic acid (0.54 g), 3-benzyl-4-fluorobenzyl alcohol (0.43 g), 4-dimethylaminopyridine (0.02 g) and dry dichloromethane (5 cm$^3$), and the resultant mixture stirred at the ambient temperature (ca. 20° C.) for 18 hours. The reaction mixture was then heated to the reflux temperature for 3 hours, and subsequently cooled again. The precipitate which formed was removed by filtration, and the filtrate concentrated by evaporation of the solvent under reduced pressure. The residual oil was purified by column chromatography using a silica column eluted with a mixture of ethyl acetate (1 part by volume) and petroleum ether (boiling range 60°-80° C., 19 parts by volume), to yield 3-benzyl-4-fluorobenzyl (1RS, cis)-3-(Z-2-chloro-3,3,3-trifluoroprop-1-en-1-yl)-2,2-dimethylcyclopropanecarboxylate (0.32 g).

$^1$H NMR (CDCl$_3$) ppm: 1.20 (s,3H); 1.22 (s,3H); 2.0 (d, J=7 Hz, 1H); 2.20 (t,J=7 Hz,1H); 4.05 (s,2H); 5.08 (s,2H); 6.90-7.40 (m,9H).

$^{19}$F NMR (ppm-relative to: −69.1(s); −118.6(m). CFCl$_3$).

Infra red (liquid film): 2975, 2940, 1730, 1660, 1605, 1505, 1140, 960, 820 cm$^{-1}$.

EXAMPLE 3

This Example illustrates the preparation of (RS)-α-cyano-3-benzyl-4-fluorobenzyl (1RS, cis)-3-(Z-2-chloro-3,3,3-trifluoroprop-1-en-1-yl)-2,2-dimethylcyclopropanecarboxylate (Product II).

Thionyl chloride (5 cm$^3$) was slowly added to (1RS, cis)-3-(Z-2-chloro-3,3,3-trifluoroprop-1-en-1-yl)-2,2-dimethylcyclopropane carboxylic acid (1 g) at 0° C. The stirred mixture was then heated to the reflux temperature for 30 minutes, and then allowed to cool to the ambient temperature (ca. 20° C.). The reaction mixture was diluted with toluene (15 cm$^3$), and the solvent removed by evaporation under reduced pressure. This cycle was repeated twice more, until all traces of residual thionyl chloride had been removed. The crude intermediate acid chloride was then immediately dissolved in 20 cm$^3$ of a mixture of diethyl ether (3 parts by volume) and petroleum ether (boiling range 40°-60° C., 1 part by volume). 3-Benzyl-4-fluorobenzaldehyde (0.86 g) was then added to the solution, followed by a solution of sodium cyanide (0.20 g) and tetra-n-butyl ammonium bromide (0.03 g) in water (2 cm$^3$). The two-phase reaction mixture was then vigorously stirred for 18 hours at the ambient temperature. After dilution with ethyl acetate, the organic layer was separated and washed with aqueous sodium bicarbonate solution and brine, and dried over magnesium sulphate. Removal of the solvents by evaporation under reduced pressure gave an oil, which was subjected to purification by column chromatography using a silica gel column eluted with a mixture of ethyl acetate (1 part by volume) and petroleum ether (boiling range 40°-60° C., 9 parts by volume) to yield (RS)-α-cyano-3-benzyl-4-fluorobenzyl (1RS, cis)-3-(Z-2-chloro-3,3,3-trifluoroprop-1-en-1-yl)-2,2-dimethylcyclopropane carboxylate (0.86 g 46%) as a mixture of diastereoisomers.

$^1$H NMR (CDCl$_3$) (ppm): 1.30 (s,6H); 2.0 (d,J=7 Hz,1H); 2.24 (t,J=7 Hz,1H); 4.00 (s,2H); 6.28, 6.32 (2d,1H); 6.80 (d,J=7 Hz,1H); 7.10-7.40 (m,8H).

$^{19}$F NMR (ppm-relative to: −69.3(s), −114.6(m). CFCl$_3$).

Infra red (liquid film): 2980, 1745, 1660, 1605, 1505, 1135, 820 cm$^{-1}$.

EXAMPLE 4

The following compounds were prepared from the appropriate starting material according to the method of Example 2 or Example 3.

(i) 3-Benzyl-4-fluorobenzyl (1RS,cis/trans)-3-(2,2-difluoroethenyl)-2,2-dimethylcyclopropanecarboxylate, cis:trans ratio of 1:9 (Product III), using the method of Example 2.

$^1$H NMR (CDCl$_3$) (ppm): 1.13 (3H,s); 1.22 (3H,s); 1.44 (1H,d); 1.90 (1H,m); 4.0 (2H,s); 4.0-41. (1H,m); 5.0 (2H,s); 6.8-7.5 (8H,m).

GLC retention time: 8.37, 8.63 minutes.

(ii) 3-Benzyl-4-fluorobenzyl (1RS,tans)-3-(2,2-dichloroethyenyl)-2,2-dimethylcyclopropanecarboxylate (Product IV), using the method of Example 2.

$^1$H NMR (CDC13) (ppm): 1.17 (3H,s); 1.22 (3H,s); 1.61 (1H,d); 2.24 (1H,m); 4.00 (2H,s); 5.02 (2H,s); 5.6 (1H,d); 7.0-7.4 (8H,m).

GLC retention time: 10.93 minutes.

(iii) 3-Benzyl-4-fluorobenzyl (1R,cis)-3-(Z-2-chloro-3,3,3-trifluoroprop-1-en-1-yl)-2,2-dimethylcyclopropanecarboxylate (Product V), by the method of Example 2.

$^1$H NMR (CDC13) (ppm): 1.25 (6H,m); 1.98 (12H,m); 2.15 (1H,m); 4.0 (2H,s); 5.0 (2H,s); 6.8-7.4 (9H,m).

GLC retention time: 9.61 minutes.

(iv) (RS)-α-Cyano-3-benzyl-4-fluorobenzyl (1R,cis)-3-(Z-2-chloro-3,3,3-trifluoroprop-1-en-1-yl)-2,2-dimethylcyclopropanecarboxylate (Product VI), by the method of Example 3.

$^1$H NMR (CDCl$_3$) (ppm): 1.1-1.4 (6H,m); 2.0 (1H,d); 2.24 (1H,m); 4.02 (2H,s); 6.29, 6.32 (1H,2s); 6.8 (1H,d); 7.0-7.4 (8H,m).

(v) 3-Benzyl-4-fluorobenzyl 2,2,3,3-tetramethylcyclopropanecarboxylate (Product VII) by the method of Example 2.

$^1$H NMR (CDCl$_3$) (ppm): 1.17 (6H,s); 1.21 (6H,s); 4.0 (2H,s); 5.0 (2H,s); 7.0 (8H,s).

GLC retention time: 8.85 minutes.

(vi) 3-Benzyl-4-fluorobenzyl (1RS,cis/trans)-3-(2-methylprop-1-en-1-yl)-2,2-dimethylcyclopropanecarboxylate, cis:trans ratio 3:7, (Product VIII) by the method of Example 2.

$^1$H NMR (CDCl$_3$) (ppm): 1.12 (3H,s); 1.23 (3H,s); 1.18 (3H,s); 1.20 (3H,s); 1.4 (1H,d); 1.69 (6H,m); 2.05 (1H,m); 4.0 (2H,s); 5.0 (2H,s); 4.9 (1H,d); 6.8-7.4 (8H,m).

GLC retention time: 9.81, 9.92 minutes.

(vii) 3-Benzyl-4-fluorobenzyl (1RS,trans)-3-(2-trifluoromethyl-3,3,3-trifluoroprop-1-en-1-yl)-2,2-dimethylcyclopropanecarboxylate (Product IX), by the method of Example 2.

$^1$H NMR (CDCl$_3$) (ppm): 1.19, 1.21 (6H,2s); 1.82 (1H,d); 2.40 (1H,m); 3.92 (2H,s); 4.98 (2H,s); 6.24 (1H,d); 6.8-7.2 (8H,m).

GLC retention time: 8.64 minutes.

Note: this product contains less than 10% of the (1RS,cis) isomer due to the presence of (1RS,cis) material in the starting acid.

(viii) 3-Benzyl-4-fluorobenzyl (1RS,cis/trans)-3-(2,2-dibromoethenyl)-2,2-dimethylcyclopropanecarboxylate, cis:trans ratio 4:1, (Product X), by the method of Example 2.

$^1$H NMR (CDCl$_3$) (ppm): 1.24 (6H,s); 1.9 (1H,m); 4.0 (2H,s); 5.01 (2H,s); 6.8 (1H,d); 7.0–7.4 (8H,m).

GLC retention time: 11.73, 11.82 minutes.

(ix) 3-Benzyl-4-fluorobenzyl (1RS,trans)-3-[2-(1,1-dimethylethyl)pyrimidin-5-yl]-2,2-dimethylcyclopropanecarboxylate (Product XI) by the method of Example 2.

$^1$H NMR (CDCl$_3$) (ppm): 0.96 (3H,s); 1.35 (3H,s); 1.40 (9H,s); 1.99 (1H,d); 2.56 (1H,d); 4.00 (2H,s); 5.09 (2H,s); 7.2–7.4 (8H,m); 8.47 (2H,s).

(x) (RS)- α-Cyano-3-benzy-1-4-fluorobenzyl (1RS,trans)-3-[2-(1,1-dimethylethyl)pyrimidin-5-yl]-2,2-dimethylcyclopropanecarboxylate as a 3:2 mixture of enantiomer pairs (Product XII) by the method of Example 2.

Note: The preparation of (RS)-α-cyano-3-benzyl-4-fluorobenzyl alcohol is described in Example 6.

$^1$H NMR (CDCl$_3$) (ppm): 1.0 (3H,2s); 1.3, 1.4 (3H,2s); 1.4 (9H,2s); 2.0 (1H,2d); 2.6 (1H,2d); 4.25 (2H, broad s); 6.4 (1H,2s); 6.9–7.4 (8H,m); 8.45, 8.50 (2H,2s).

GLC retention time: 14.60, 15.25 minutes.

(xi) (RS)-α-Methyl-3-benzyl-4-fluorobenzyl (1RS,cis)-3-(Z-2-chloro-3,3,3-trifluoroprop-1-en-1-yl)-2,2-dimethylcyclopropanecarboxylate (Product XIII) by the method of Example 2.

Note: The preparation of (RS)-α-methyl-3-benzyl-4-fluorobenzyl alcohol is described in Example 5.

400MHz $^1$H NMR (CDCl$_3$) (ppm): 1.0–1.6 (9H,m); 1.95 (1H,2d); 2.13 (1H,m); 3.99 (2H,s); 5.8 (1H,m); 6.85 (1H,m); 6.95–7.4 (8H,m).

GLC retention time: 9.23, 9.36 minutes.

EXAMPLE 5

This Example illustrates the preparation of (RS)-α-methyl-3-benzyl-4-fluorobenzyl alcohol.

A solution of methylmagnesium bromide (0.989 g) in dry tetrahydrofuran (2.77 cm$^3$) was added to a stirred solution of 3-benzyl-4-fluorobenzaldehyde (0.89 g) in dry tetrahydrofuran under an atmosphere of nitrogen, the temperature of the reaction mixture being kept at −35° C. during the addition by external cooling. The mixture was allowed to warm to the ambient temperature and stirred for 90 minutes. The mixture was then cautiously added to water and the products extracted into ethyl acetate. The combined organic layers were washed with water and brine, then dried over anhydrous magnesium sulphate. Evaporation of the solvent under reduced pressure gave the title compound (0.93 g), 97% pure by GLC analysis.

90 MHz $^1$H NMR (CDCl$_3$) (ppm): 1.35 (3H,d); 3.9 (2H,s); 4.7 (1H,q); 6.8–7.4 (8H,m).

GLC retention time: 5.41 minutes.

EXAMPLE 6

This Example illustrates the preparation of (RS)-α-cyano-3-benzyl-4-fluorobenzaldehyde.

3-Benzyl-4-fluorobenzaldehyde (0.5 g) was dissolved in glacial acetic acid (10 cm$^3$) and the solution cooled in an ice bath. A solution of potassium cyanide (0.26 g) in water (2 cm$^3$) was added dropwise to the stirred, cooled solution and stirring continued for 30 minutes. The mixture was allowed to warm to the ambient temperature (ca. 20° C.) and stood for 16 hours, at which time analysis by thin layer chromatography showed mainly unreacted aldehyde. Further acetic acid (5 cm$^3$) was added to redissolve the precipitate which had formed on standing and a further solution of potassium cyanide (0.26 g) in water (1 cm$^3$) was added. The mixture was allowed to stand for 1 week at the ambient temperature, and was then diluted with water. The aqueous mixture was shaken with diethyl ether and the ether layers separated and washed with aqueous sodium bicarbonate solution and brine, then dried over anhydrous magnesium sulphate. Evaporation of the solvent under reduced pressure gave a mixture of the starting aldehyde and the expected cyanohydrin in equal proportions (0.5 g) as a yellow solid. The title compound (0.24 g) was isolated as the second fraction obtained by column chromatography on silica gel, eluting with petroleum ether (boiling range 40°–60° C.) containing 40% by volume diethyl ether.

$^1$H NMR (CDCl$_3$) (ppm): 4.05 (3H,2s); 5.45 (1H,s); 7.0–8.0 (8H,m).

EXAMPLE 7

This Example illustrates the biological activity of the compounds according to the invention.

The activity of the Product was determined using a variety of insect pests. The Product was used in the form of liquid preparations containing from 100 to 500 parts per million (ppm) by weight of the Product. The preparations were made by dissolving the Product in acetone and diluting the solutions with water containing 0.1% by weight of a wetting agent sold under the trade name "SYNPERONIC" NX until the liquid preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

In the case of the species *Musca domestica* (housefly), an additional assessment to determine the knockdown effect of the compounds was performed. Details are given in Table II.

The results of the tests are given in Table III for each of the Products, at the rate in parts per million given in the second column, as a grading of mortality designated as A, B or C wherein A indicates 80–100% mortality or knockdown, B indicates 50–79% mortality or knockdown and C indicates less than 50% mortality or knockdown.

In Table III the pest organism used is designated by a letter code and the pests species, the support medium or food, and the type and duration of test is given in Table II.

TABLE II

| CODE LETTERS (Table IV) | TEST SPECIES | SUPPORT MEDIUM/FOOD | TYPE OF TEST | DURATION (days) |
|---|---|---|---|---|
| TUa | *Tetranychus urticae* (spider mites - adults) | French bean leaf | Contact | 3 |
| TUe | *Tetranychus urticae* (spider mites - ova) | French bean leaf | Contact | 6 |
| MP | *Myzus persicae* (aphids) | Chinese Cabbage leaf | Contact | 3 |
| NC | *Nephotettix cincticeps* (green leaf hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/maize seed | Residual | 3 |
| BG | *Blattella germanica* (cockroach nymphs) | Plastic pot | Residual | 3 |
| MD | *Musca domestica* (houseflies - adults) | Cotton wool/sugar | Contact | 1 |
| MD/KD | *Musca domestica* (houseflies - adults) | Cotton/wool sugar | Knockdown | 4 hours |
| SP | *Spodoptera exigua* (lesser army worm - larvae) | Cotton leaf | Residual | 3 |

"Contact" test indicates that both pests and medium were treated and "residual" indicates that the medium was treated before infestation with the pests.

TABLE III

| Product | Example No. | Rate | $TU_a$ | $TU_e$ | MP | NC | MD/KD | MD | BG | HV | SP | DB |
|---|---|---|---|---|---|---|---|---|---|---|---|---|
| I | 2 | 500 | A | A | A | — | A | A | A | A | A | A |
| II | 3 | 500 | A | A | A | — | A | A | A | A | A | A |
| III | 4(i) | 100 | B | C | A | — | A | A | C | A | A | A |
| IV | 4(ii) | 100 | C | C | A | A | A | A | C | A | A | A |
| V | 4(iii) | 500 | A | A | A | A | A | A | — | A | A | A |
| VI | 4(iv) | 100 | A | C | A | A | A | A | A | A | A | A |
| VII | 4(v) | 500 | — | C | A | — | A | A | A | A | C | A |
| VIII | 4(vi) | 500 | C | C | A | — | A | A | C | A | A | A |
| IX | 4(vii) | 500 | A | C | A | — | A | A | A | A | A | A |
| X | 4(viii) | 500 | — | C | A | — | A | A | A | A | A | A |
| XI | 4(ix) | 500 | A | A | A | — | B | B | C | A | A | A |
| XII | 4(x) | 500 | A | B | B | — | A | C | C | C | C | A |
| XIII | 4(xi) | 500 | A | — | A | A | A | A | A | A | A | A |

I claim:

1. A compound of formula

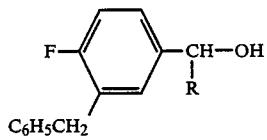

wherein R is selected from cyano and ethynyl.

2. A compound of formula

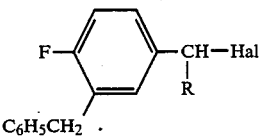

wherein R is selected rom hydrogen, cyano, methyl and ethynyl, and Hal represents a halogen atom.

3. 3-Benzyl-4-fluorobenzaldehyde.
4. 3-Benzyl-4-fluorobenzyl chloride.
5. α-Cyano-3-benzyl-4-fluorobenzyl alcohol.
6. α-Cyano-3-benzyl-4-fluorobenzyl chloride.
7. α-Methyl-3-benzyl-4-fluorobenzyl chloride.